US00PP12433P2

(12) United States Plant Patent
Scheffers

(10) Patent No.: US PP12,433 P2
(45) Date of Patent: Mar. 5, 2002

(54) DRACAENA PLANT NAMED 'WHITE JEWEL'

(76) Inventor: Ruud A. M. Scheffers, De Plaats 9, 2675 CK Honselersdijk (NL)

( * ) Notice: Subject to any disclaimer, the term of this patent is extended or adjusted under 35 U.S.C. 154(b) by 0 days.

(21) Appl. No.: 09/326,615

(22) Filed: Jun. 7, 1999

(51) Int. Cl.[7] ..... A01H 5/00
(52) U.S. Cl. ..... Plt./383
(58) Field of Search ..... Plt./383

(56) References Cited

PUBLICATIONS

Extract from the Register of Community Plant Variety Rights, 'WHITE Jewel', filed Jan. 16, 1998, File No.: 1997/0384, European Union (Grant No. 4866).

OPOV–ROM GTITM Computer Database, 2000/04, GTI Jouve Retrieval Software, citation for cultivar name.*

* cited by examiner

*Primary Examiner*—Bruce R. Campell
*Assistant Examiner*—Susan B. McCormick
(74) *Attorney, Agent, or Firm*—Foley & Lardner

(57) ABSTRACT

A distinct Dracaena plant named 'White Jewel' characterized by its compact plant growth; leaves which are 10 inches long and 2 inches wide; distinctive leaf color with a dark green margin (RHS 135A) which is approximately 0.5 cm wide, a leaf center which is green (RHS 137B) to grey-green (RHS 191B) and approximately 3.0 to 4.5 cm wide, and between the margin and center of the leaf a white (RHS 155C) area which is apporximately 0.4 to 0.6 cm wide.

1 Drawing Sheet

BACKGROUND OF THE INVENTION

The present invention comprises a new and distinct cultivar of Dracaena plant botanically known as *Dracaena Vand. Ex. L. fragrans* (group Compacta) and hereinafter referred to by the cultivar name 'White Jewel'.

The new cultivar was selected by the inventor, Ruud A. M. Scheffers, in Honselersdijk, The Netherlands, in April of 1995. The new cultivar was obtained as a natural mutation in the form of a sport of *Dracaena Vand. Ex. L. fragrans* (group Deremensis) 'White Stripe' (unpatented).

The new cultivar was first asexually propagated by the inventor in Honselersdijk, The Netherlands, in July of 1995. Subsequent asexual reproduction of the new cultivar by division has demonstrated that the combination of characteristics as herein disclosed for the new cultivar are firmly fixed and retained through successive generations of asexual reproduction.

BRIEF DESCRIPTION OF THE INVENTION

The following traits have been repeatedly observed and in combination distinguish 'White Jewel' as a new and distinct cultivar:

1. Compact plant growth;

2. Leaves which are 10 inches long and 2 inches wide; and

3. Distinctive leaf color with a dark green margin (RHS135A) approximately 0.5 cm wide, center which is green (RHS 137B) to grey-green (RHS 191B) and approximately 3.0 to 4.5 cm wide and between the margin and center a white (RHS 155C) area which is approximately 0.4 to 0.6 cm wide.

'White Jewel' has not been observed under all possible environmental conditions. The phenotype on the new cultivar may vary significantly with variations in environment such as temperature, light intensity, and daylength without any change in genotype. The following observations, measurements and values describe plants grown in The Netherlands under greenhouse conditions which closely approximate those generally used in horticultural practice.

In comparison with the well-known Dracaena cultivar 'White Stripe', 'Wite Jewel' has shorter, wider leaves with a wider stripe at the leaf-edge. The leaves of 'White Jewel' are 10 inches long and up to 2 inches wide, whereas the leaves of 'White Stripe' are 16 inches long and 3 inches wide. The green center of 'White Stripe' is a yellow-green, between RHS 146B and 146C, whereas the green center of 'White Jewel' is a grey-green, RHS 137B to RHS 191 B. In addition, 'White Jewel' is more compact than 'White Stripe'.

BRIEF DESCRIPTION OF THE DRAWING

The accompanying photograph illustrates a 10-week old plant of Dracaena 'White Jewel' in a 4¾-inch pot, with colors being as true as possible with illustrations of this type.

DETAILED BOTANICAL DESCRIPTION

The age of the plants described is 4 months old, as grown in The Netherlands.

Color references are made to The Royal Horticultural Society Colour Chart (R.H.S.), except where general colors of ordinary significance are used. Colors are approximate as color depends on horticultural practices such as light level and fertilization rate, among others.

Classification:

*Botanical.*—*Dracaena Vand. Ex. L. fragrans* (group Compacta).

*Commercial.*—Dracaena 'White Jewel'.

Parentage: Mutant of *Dracaena Vand. Ex. L. fragrans* (group Deremensis) 'White Stripe'.

Propagation: Primarily by vegetative division of the plant head or apical meristem.

Plant habit:

*Growth rate.*—Medium to fast; approximately 20 weeks to obtain a mature plant after taking a cutting and rooting it.

*Vigor.*—It takes 4 months for the plant to grow into a fully mature plant with a plant height of 38–40 cm.

*Form.*—Compact.

*Plant height.*—Approximately 10 inches when grown in a 4¾-inch pot for 150 days in The Netherlands. A mature plant is 38–40 cm in height.

*Plant width.*—Approximately 14 inches when grown in a 4¾-inch pot for 150 days in The Netherlands.

Leaves:

*Form and size.*—Narrow and elongated; approximately 10 inches long and 2.0 inches wide.

*Texture.*—Strong and leather-like.

*Veins.*—Green (RHS 139 B to RHS 139 C) in color and visible on the bottom.

*Color.*—The margin is dark green (RHS 135A) and approximately 0.5 cm in width. The center is green (RHS 137B) to grey-green (RHS 191B) and approximately 3.0 to 4.5 cm wide. Between the margin and center is a white (RHS 155C) area which is approximately 0.4 to 0.6 cm wide.

*Margin.*—Entire.

*Thickness.*—Medium.

*Number.*—Approximately 22 leaves are produced in a 4¾-inch pot after 150 days growth in The Netherlands.

Stem:

*Length.*—Short and approximately 0.5 inches long.

*Thickness.*—Approximately 0.5 inches, formed by bases of leaves.

*Color.*—Light-green to white (RHS 139B to RHS 155C).

Roots: Root initiation time is 3 weeks under Dutch growing conditions, color is orange-brown (RHS 175 A to RHS 175 B), well branched.

Plant disease and insect tolerance: No special observations made.

I claim:

1. A new and distinct cultivar of Dracaena plant named 'White Jewel', as described and illustrated herein.

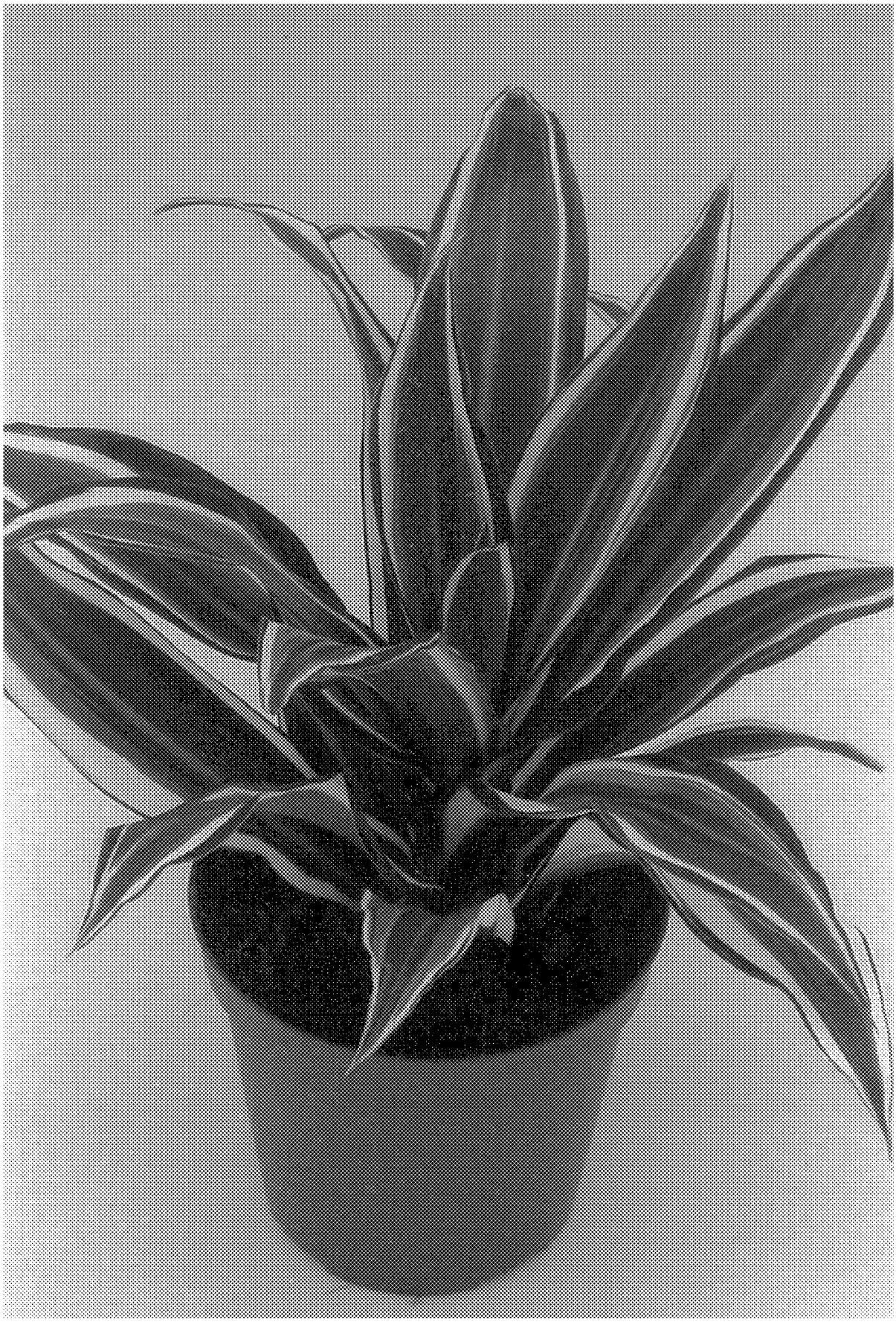

* * * * *